(12) United States Patent
Wang (10) Patent No.: US 8,389,019 B2
(45) Date of Patent: Mar. 5, 2013

(54) METHOD FOR IMPROVING THE QUALITY OF MEAT BY REDUCING BOAR TAINT

(76) Inventor: Min Wang, Columbia, MO (US)

( * ) Notice: Subject to any disclaimer, the term of this patent is extended or adjusted under 35 U.S.C. 154(b) by 496 days.

(21) Appl. No.: 12/596,349

(22) PCT Filed: Apr. 18, 2007

(86) PCT No.: PCT/US2007/066830
§ 371 (c)(1),
(2), (4) Date: Oct. 16, 2009

(87) PCT Pub. No.: WO2008/130399
PCT Pub. Date: Oct. 30, 2008

(65) Prior Publication Data
US 2010/0062103 A1    Mar. 11, 2010

(51) Int. Cl.
*A61K 33/30*    (2006.01)
*A61D 7/00*    (2006.01)
(52) U.S. Cl. .................................... 424/641; 424/643
(58) Field of Classification Search .................. None
See application file for complete search history.

(56) References Cited

U.S. PATENT DOCUMENTS

| | | | |
|---|---|---|---|
| 3,887,704 A | 6/1975 | Lichtenstein | |
| 4,339,438 A | 7/1982 | Fahim | |
| 5,372,822 A | 12/1994 | Fahim | |

FOREIGN PATENT DOCUMENTS

GB    2126478 A    3/1984

OTHER PUBLICATIONS

Material Safety Data Sheet—Zinc acetate dihydrate (Rev. Oct. 3, 2005).*

* cited by examiner

*Primary Examiner* — James H. Alstrum-Acevedo
*Assistant Examiner* — Frank Choi
(74) *Attorney, Agent, or Firm* — Grace J. Fishel (57) ABSTRACT

Disclosed is a method for reducing boar taint in pigs, said method comprising injecting a solution of a pharmaceutically acceptable zinc salt into a dorsal cranial portion of each testis of a male pig preferably when the pig is less than one week old. The solution contains at least 20 mg of zinc ion per ml of solution and the solution is injected into the testis in a volume that is contained within the testis.

9 Claims, 3 Drawing Sheets

METHOD FOR IMPROVING THE QUALITY OF MEAT BY REDUCING BOAR TAINT

All patent and non-patent references cited in the present application are hereby incorporated by reference in their entirety.

BACKGROUND OF THE INVENTION

1. Field of the Invention

The present invention relates to methods for improving the quality of meat by reducing boar taint caused by skatole and/or androstenone. The methods involve injecting zinc salts into the testis in a manner that promotes the effectiveness of the injection.

2. Brief Description of the Prior Art

The odor and flavor of pork meat is affected negatively due to the presence of skatole and/or androstenone over certain levels. The odor and flavor may be affected to such an extent that the meat is not acceptable for human consumption.

Skatole and androstenone are unrelated in their production. Androstenone, and other 16 androstenes that are found bound in boar fat, are produced in the testes with pregnenolone as the precursor (Brooks and Pearson, 1989). These compounds are released into the blood via the spermatic vein and are stored in fat (Bonneau and Terqui, 1982). The 5-alpha-androst-16-en-3-one configuration is the predominant storage form because it is the most lipophilic and it is therefore the major component responsible for boar taint (Claus, 1979). During sexual stimulation these steroids can be released back into the bloodstream to travel to the submaxillary gland for use as an important pheromone in saliva (Gower, 1972; Claus, 1979). It is apparent that this storage procedure is also reversible over time because after castration of older males, steroid concentrations in adipose tissue decline (Claus, 1976).

The levels of androstenone found in boar fat vary widely and are affected by age, weight, genetics and stage of sexual maturity (Jonsson and Andresen, 1979; Bonneau, 1981; Willeke, 1980; Walstra, 1984). Additionally, they may be sensitive to external stimuli such as rearing environment or sexual exposure although the literature is somewhat conflicting. As a general rule androstenone production begins increasing slowly when the animal reaches about 70 kg or approximately 4 months of age (Bonneau, 1981). It is also known that the highest incidence of objectionable odor in fat occurs in boars weighing over 95 kg and greater than 5 months of age (Walstra, 1984).

The other component in boar taint is skatole. It is produced by lactobacilli in the hindgut of the pig as these microorganisms break down tryptophan (Yokoyama and Carlson, 1979). Skatole concentration can be altered somewhat by diet and is normally found in excess of threshold levels (0.20 ppm) in boars. However, these levels are rarely reached in barrow or gilt fat (Mortensen et al., 1986) even though gut microflora differs only slightly between the sexes. This may indicate a hormonal influence either in the absorption rate of skatole or the rate of storage and degradation once absorbed (Lundstrom et al., 1988).

Historically, surgical castration has been the choice of most swine producers to deal with boar taint. Surgical castration is commonly carried out by the farmer during the first week of a male pig's life without sedation or anesthetics. The testes of a pig are filled with nerves and, for reasons of animal welfare, it is expected that surgical castration of piglets without anesthesia will be forbidden in the near future, at least in the EU area. In Norway such castration is forbidden from 2009. In the interim period, authorized veterinarians can only perform castration which makes costs prohibitively high for industrial scale pig farming.

Other methods have been tried to overcome the problems associated with surgical castration. For example, intact males have been treated with progestagen either through an implant or in the diet (Berger et al., 1981; Kluber et al., 1988). Immunization of boars against one of the compounds responsible for boar taint has also been tried. (Williamson et al., 1985; Brooks et al., 1986). Both of these methods have serious problems: hormonal treatment must be repeated several times and is not acceptable in swine for human consumption in some cultures. Immunization is not uniformly effective in all animals and there is some risk that cross-reacting antibodies will be induced causing undesired side effects.

In view of the problems with surgical, hormonal and immunocastration, there is a continuing need for an improved method of castration that controls boar taint. The present invention relates to a method of chemical castration and accomplishes those goals.

By way of review, there are two approaches to chemical castration, the first being to inject a sclerotic agent into the vas deferens of an intact male causing an occlusion in the duct blocking the transport of sperm and rendering the animal infertile. This type of chemical sterilization induces infertility but does not reduce the production of testosterone or other testicular steroids responsible for boar taint and male aggressiveness. Many compounds have been shown effective for this purpose: 10 percent silver nitrate or 3 percent formalin (Pineda et al., 1976); 95 percent ethanol (Freeman and Coffee, 1973); dondren (Bierschwal and Ebert, 1961); and quinacrine (Malaviya et al., 1974).

The second type of chemical castration and the type employed in the present invention involves an agent responsible for tissue modification and subsequent disruption of testicular function. The particular effect observed depends on the chemical and concentration injected, species, maturity of the animal and so forth. Background work is described in U.S. Pat. Nos. 4,156,427 and 4,339,438 to Fahim wherein the use of zinc tannate is described and U.S. Pat. No. 5,070,080 to Fahim wherein the use of a neutralized solution of a mineral gluconate and amino acid is described. U.S. Pat. No. 5,372,822 to Fahim describes the use of zinc acetate to control boar taint.

The volume of chemical sterilant that can be injected into a testis is limited because a testis is a closed body. In the above-mentioned patents to Fahim, the chemical sterilant was injected into the midline or bottom of the testis. As mentioned above, the effect on testicular function depends on the chemical nature and concentration of the material injected, hence a method that promotes the effectiveness of the injection such that an effective dose to control boar taint may be delivered in a volume that can be received in the testis is needed.

BRIEF SUMMARY OF THE INVENTION

In view of the above, it is an object of the present invention to provide a method for reducing boar taint in pigs which avoids the problems associated with surgical, hormonal and immunocastration. Another object is to provide a method for injecting zinc salts into the testis in a manner that promotes the reduction of boar taint. Other objects and features of the invention will be in part apparent and in part pointed out hereinafter.

In accordance with the invention, a method for reducing boar taint in pigs comprises injecting a solution of a soluble pharmaceutically acceptable zinc salt into a dorsal cranial portion of each testis of a male pig. The solution contains at least 20 mg of zinc ion per ml of solution and the solution is injected into the testis in a volume that is contained within the testis. Male pigs may be injected within the first days of life without anesthesia.

The invention summarized above comprises the methods hereinafter described, the scope of the invention being indicated by the subjoined claims.

DETAILED DESCRIPTION OF THE INVENTION

Testicular Structure and Function

Figure 1:
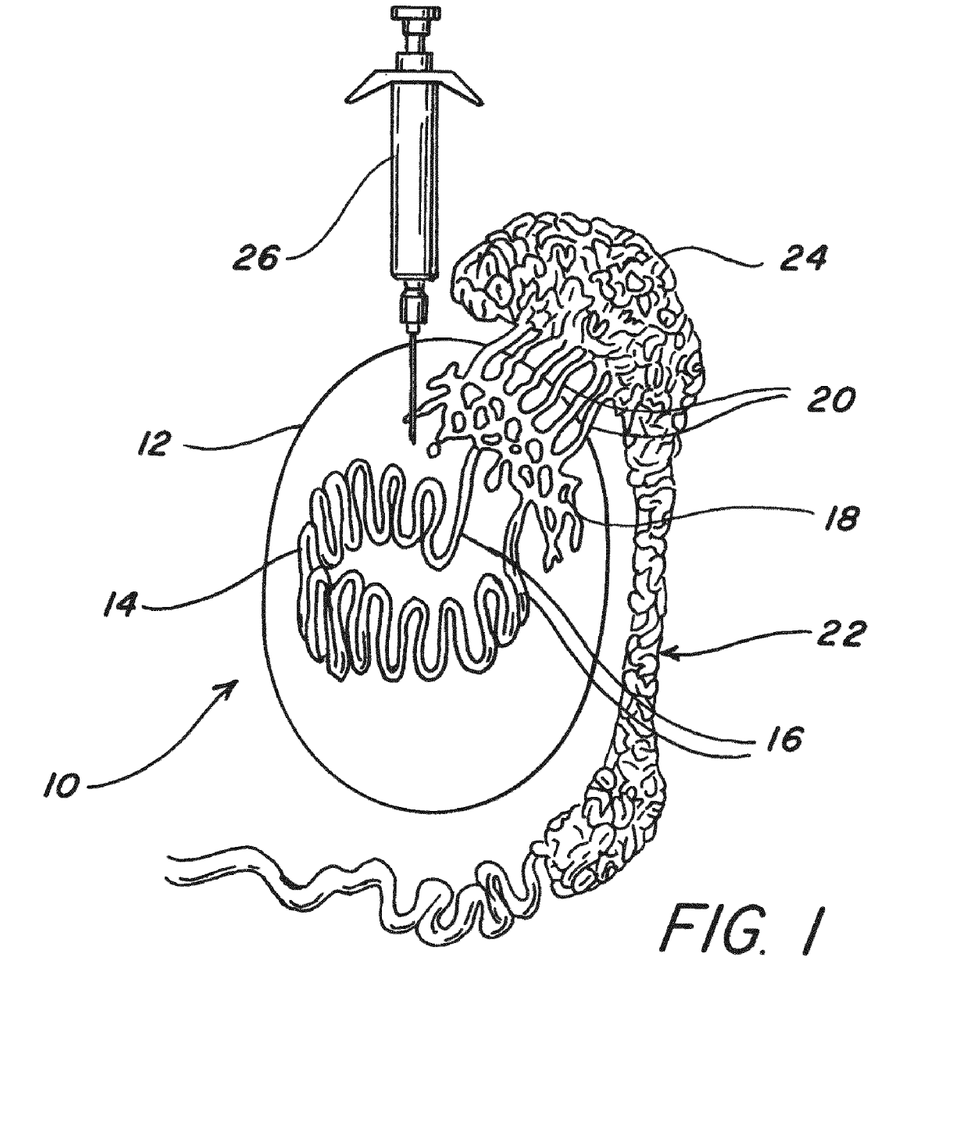
FIG. 1 is a schematic representation of a scrotal testis in cross-section.

As shown in FIG. 1 testis 10 has an oval structure with an outer covering, the fibrous tunica albuginea 12, thickened posteriorly along the epididymal border, where it forms the mediastinum. Fibrous septa extend between the mediastinum and the tunica albuginea to divide each testis into compartments enclosing one or more seminiferous tubules 14. Sperm are produced in the seminiferous tubules 14.

Each seminiferous tubule 14 is lined on its inside by the seminiferous epithelium, which contains two kinds of cells—male germ cells and Sertoli cells. Sperm develop in the seminiferous tubules 14 from less mature cell types. The least mature germinal cells, the spermatogonia, divide to form primary spermatocytes. The primary spermatocytes divide meiotically to form secondary spermatocytes which, in turn, divide mitotically to form spermatids. Spermatids do not divide further, but undergo a complicated metamorphosis in the process of forming sperm. The Sertoli cells nurture the spermatids and secrete a fluid that washes the sperm along the seminiferous tubules 14. The seminiferous tubules 14 are circular in cross-section and regions exist outside the tubules. These interstitial spaces contain blood vessels and Leydig cells which synthesize and secrete testosterone.

The seminiferous tubules 14 form loops, the two terminal portions of which connect with the tubuli recti 16. Sperm, suspended in testicular fluid, leave the seminiferous tubules and enter the tubuli recti 16. These tubules, in turn, join the rete testis 18 which is a network of tubules within the testis 10. At the upper end of the mediastinum, the vessels of the rete testis 18 terminate in the ductuli efferentes 20 which pass through the tunica albuginea 12 and carry the seminal fluid from the testis to the epididymis 22. The passage of sperm through the seminiferous tubules 14, tubuli recti 16, rete testis 18 and ductuli efferentes 20 is passive. The cells lining these ducts have cilia and the beating of these hairlike structures moves the fluid and the suspended sperm through the ducts and into the head of the epididymis 24.

The sperm produced in the seminiferous tubules 14 must undergo a series of changes before they are capable of fertilizing an egg. The journey starts with safe passage through the tubuli recti 16, rete testis 18, ductuli efferentes 20 into the head of the epididymis 24. The epithelium of the tubuli recti 16 and rete testis 18 add fluids which are then reabsorbed by the epithelium in the ductuli efferentes 20. The composition of the fluids in the tubuli recti 16, rete testis 18 and ductuli efferentes 20 is regulated and essential to the provision of viable cells to the epididymis 22 for further processing into mature sperm.

Chemical Sterilant

For use in accordance with the present invention, the chemical sterilant is a pharmaceutically acceptable zinc salt or mixture of such salts capable of forming a water solution delivering at least 20 mg of zinc ion per 1 ml. If not neutral when formed, the solution may be buffered to a pH in the range of 6.0 to 7.5 such that it may be injected intratesticularly.

As used herein, "pharmaceutically acceptable zinc salt" refers to a salt that does not impart any undesired toxicological effects. By "undesired toxicological effect" is meant an $LD_{50}$ of greater than 500 mg/kg in rats. Examples of such salts include, but are not limited to, salts formed with organic acids. Such salts include zinc acetate and zinc propionate. Other candidate organic salts with somewhat lower levels of solubility and dissociation, include zinc butyrate, zinc formate, zinc gluconate, zinc glycolate and zinc lactate. The solubility of zinc gluconate can be increased by adding glycine or certain other amino acids as described in U.S. Pat. No. 4,937,234 to Fahim. Zinc salts formed with organic acids such as, for example, oxalic acid, tartaric acid, succinic acid, maleic acid, tannic acid, etc. also are possible candidates if sufficiently soluble in water and non-toxic. Zinc salts formed with inorganic acids, for example, hydrochloric acid, hydrobromic acid, sulfuric acid, phosphoric acid, nitric acid and the like are also candidates if they meet the requirements of solubility and lack of undesired toxicological effects as set forth above.

The preferred solvent is water but the solution may also contain alcohol and other non-interfering amounts of pharmaceutically and physiologically acceptable bactericides, stabilizers and so forth commonly found in injectable compositions.

Method of Administration

It is desirable to inject the lowest possible effective amount of chemical sterilant into the testis 10 to affect the production of skatole and/or androstenone. In the case of piglets no more than 7 days old, the required dose is between about 10 and 30 mg of zinc ion per testis. A pig's testes increases in size rapidly during the early stages of development and by 4 to 4½ months of age, a dose of 50 to 150 mg of zinc ion per testes may be required. For older pigs or pigs with bigger testes, a dose as large as 250 to 800 mg of zinc ion per testes may be required with injection occurring several weeks before slaughter for the boar taint to dissipate from the carcass.

Since the volume of chemical sterilant that can be injected into a testis is limited because a testis is a closed body, the importance of zinc salt solubility is apparent. The maximum volume that can be injected correlates with testicular size and may be determined empirically. In the case of piglets no more than 7 days old, the above amount of zinc ion must be contained in a volume of about 0.2 ml for injection into each testis. Pigs 4 to 4½ months can tolerate an injection of 0.5 ml and older pigs or pigs with larger testes even larger volumes.

The locus of the injection into the testes is important. When the zinc salt is injected from the side or bottom of the testis, occasionally a portion of the testis is left intact after treatment. It has now been found that injecting 26 the zinc salt solution into the dorsal cranial portion of the testis beside the epididymis 22 has a more profound effect on the production of skatole and androstenone than injection into the midline or bottom of the testis.

The following examples illustrate the invention. While examples 2 and 4-7 are with animals other than pigs, similar results are expected with pigs.

EXAMPLE 1

A study will be made on a population of intact newborn piglets 1 to 3 days of age. On day 1 to 3, one group of the piglets will be subjected to a conventional surgical bilateral castration. Surgery will be performed under local anesthesia.

A second group will be injected into the dorsal cranial portion of each testis with 0.2 ml of a water solution of zinc acetate such that about 0.20 mg of zinc ion is delivered into each testis. A third group of the piglets will be injected with 0.5 ml of a water solution of zinc acetate such that about 0.20 mg of zinc ion is delivered into each testis. The piglets in the second and third groups will not be sedated prior to injection. The scrotal area will be thoroughly cleaned and the injections made by deep intratesticular dorsal-cranial injection using a sterile syringe. A fourth group will be intact males. After treatment, the piglets will be left with their mother until weaned. The animals in the groups will be finished, slaughtered and the meat quality compared.

EXAMPLE 2

A beagle puppy weighing 19 lbs at six months of age was injected in each testis with 0.25 ml of a chemical sterilant containing 13.1 mg/ml of zinc as zinc gluconate neutralized by 34.8 mg/ml of l-arginine with the pH adjusted to 7.0 with hydrochloric acid. The injection was into the dorsal cranial portion of the testis as could best be estimated externally.

Figure 3:
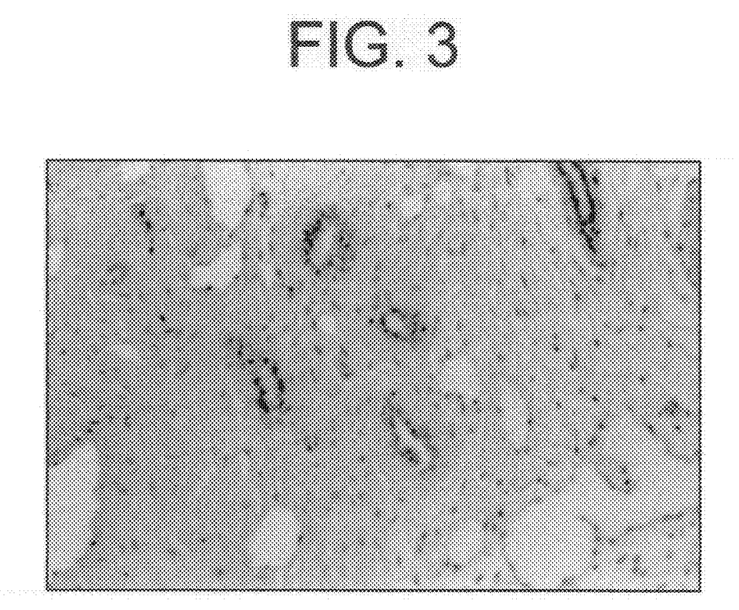
FIG. 3 is a light micrograph showing a histological section of a rete testis from a dog after treatment with the chemical sterilant described in U.S. Pat. Nos. 4,937,234 and 5,070,080 to Fahim when injected into the dorsal cranial portion of the testis.

The treated animal was sacrificed at 30 months of age when he weighed 31 lbs. The testes were excised and each weighed 3.5 g. A histological section of the rete testis was taken and a light micrograph of the section at 10× is shown in FIG. 3.

Figure 2:
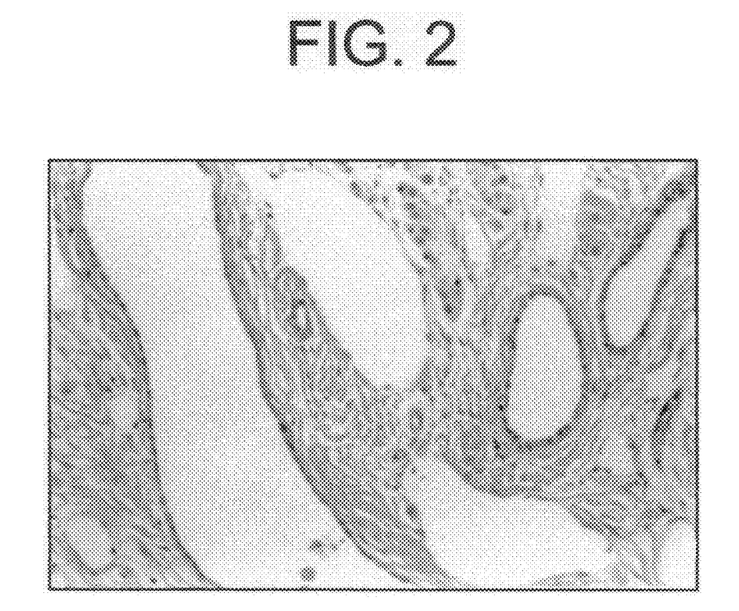
FIG. 2 is a light micrograph showing a histological section of a rete testis from a control dog.

A control beagle weighing 18 lbs at six months was housed with the treated animal. This animal was also sacrificed at 30 months. The control dog weighed 30 lbs and each testis weighed 6.8 g. A histological section of the rete testis of the control animal was taken and a light micrograph of the section at 10× is shown in FIG. 2.

EXAMPLE 3

Figure 4:
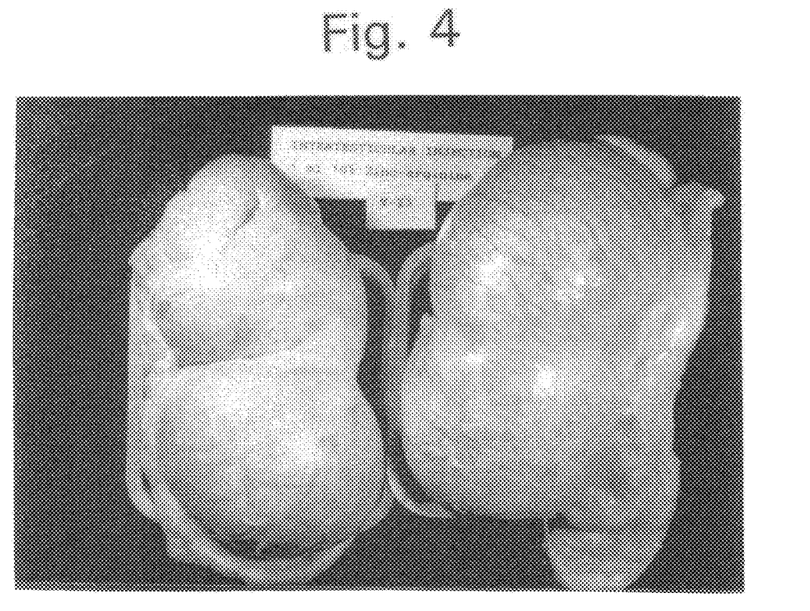
FIG. 4 is a photograph of the testes of a pig after a zinc salt is injected into the midline of the testes showing disproportional shrinkage (i.e., testes have an hourglass shape); and, FIG. 5 is a photograph of the testes of a pig after a zinc salt is injected into the dorsal cranial portion of the testis showing proportional shrinkage.
Figure 5:
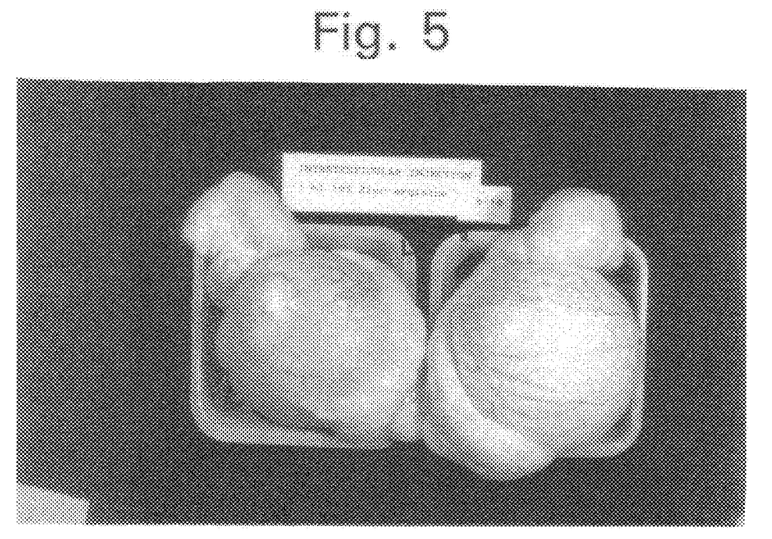

FIG. 4 shows disproportional shrinkage following injection of 1 ml of a 10% by weight solution of zinc arginine into each testis of a male pig. FIG. 5 shows proportional shrinkage following injection of the same chemical sterilant in the same amount into each testis of a male pig. A comparison of FIGS. 4 and 5 demonstrates that a different pattern of testicular shrinkage occurs with injection at the dorsal cranial area of the testes (FIG. 5) as compared to injection at the midline of the testes (FIG. 4).

EXAMPLE 4

Twenty (20) Sprague Dawley, male rats were divided into two groups of ten (10) rats per group. Group 1 rats were injected at the dorsal cranial area of the testes with 0.1 ml 10% zinc gluconate neutralized by arginine per testis. Group 2 rats were injected at the midline of the testes with 0.1 ml 10% zinc gluconate neutralized by arginine per testis. Two months post-injection, both groups were sacrificed, and all of the epididymides and testes were evaluated by histopathology.

Results showed the following,
1. Infertility/sterility was achieved in 100% of Group 1 rats (dorsal cranial injection); no sperm were found in the epididymides and there was complete dysfunction in the testes.
2. Infertility/sterility was achieved in only 70% of Group 2 rats (midline injection); sperm were found in 30% of the epididymides and some parts of the testes were functioning.

EXAMPLE 5

Forty (40) healthy, male Beagle puppies, six months of age, were divided into the following four groups according to testicular width. All four groups were injected at the dorsal cranial area of the testes.

Group 1: Control placebo injected intratesticularly with bacteriostatic water for injection containing the preservatives, methyl paraben (0.18%) and propyl paraben (0.02%).
Group 2: Injected intratesticularly with 25 mg zinc gluconate neutralized by arginine per testis
Group 3: Injected intratesticularly with 30 mg zinc gluconate neutralized by arginine per testis
Group 4: Injected intratesticularly with 35 mg zinc gluconate neutralized by arginine per testis None of the treatments affected body homeostasis. The body weight of all dogs increased. There was no clinical effect on rectal temperature; complete blood count (red blood cells, white blood cells, packed cell volume, hemoglobin, neutrophils, lymphocytes, monocytes, eosinophils, basophaphils, band neutrophils); or blood chemistries (glucose, urea, nitrogen, sodium, potassium, albumin, total protein, calcium, phosphorus, alanine aminotransferase, alkaline phosphatase, albumin/globulin ratio, creatinine).

There was transient testicular swelling of the testes in treated dogs for one week post-injection. Thereafter, testicular measurement of treated animals decreased significantly (p<0.0001) while testicular measurement of control placebo animals increased. As compared to the control placebo group, serum testosterone level at twelve (12) months post-injection had (1) decreased by 43% in the 25 mg treated group, (2) decreased by 55% in the 30 mg treated group, and (3) decreased by 52% in the 35 mg treated group.

Semen analysis was performed on a monthly basis for 21 months. Semen analysis at 24 months post-injection indicated the following.

TABLE 1

Semen Analysis of Control Placebo Dogs (n = 10)

| Active Sperm | Volume of Ejaculation | 3.25 ml |
|---|---|---|
| | Motility | 90.00% |
| | Concentration/ml (×$10^6$) | 168.90 |
| | Normal Sperm | 86.40% |

TABLE 2

Semen Analysis of 25 mg Treated Dogs (n = 10)

| 10% Severe Oligospermia | Volume of Ejaculation | 0.74 ml |
|---|---|---|
| | Motility | 1.00% |
| | Concentration/ml (×$10^6$) | 0.01 |
| | Normal Sperm | 6.70% |
| 90% Permanently Sterilized | Azoospermia (no spermatozoa in the ejaculate) | |
| | Aspermia (no semen ejaculated) | |

TABLE 3

Semen Analysis of 30 mg Treated Dogs (n = 10)

| 100% Permanently Sterilized | Azoospermia (no spermatozoa in the ejaculate) Aspermia (no semen ejaculated) |
|---|---|

TABLE 4

Semen Analysis of 35 mg Treated Dogs (n = 10)

| 100% Permanently Sterilized | Azoospermia (no spermatozoa in the ejaculate) Aspermia (no semen ejaculated) |
|---|---|

Of the ten control placebo dogs, seven copulated with females and pregnancy occurred in all of the females (100% pregnancy rate). Each of the treated dogs was exposed to three different females in heat. Two of the ten 25 mg treated dogs, five of the ten 30 mg treated dogs, and four of the ten 35 mg treated dogs copulated with females and no pregnancy occurred.

Quantitative information provides the strongest evidence that control and treated tissues are either alike or different. In order to obtain the very detailed information about the testes after dorsal cranial injection, quantitative evaluation of the testes histopathology was performed in 40 dogs post-injection. Results are presented in the following table.

TABLE 5

Summary of Quantitative Evaluation of Testis Histopathology (n = 10 per group)

| Animal Group | Basement Membrane (μm) | | | Diameter of Seminiferous Tubule (μm) | | | Height of Germinal Epithelium (μm) | | |
|---|---|---|---|---|---|---|---|---|---|
| | Right | Left | Average | Right | Left | Average | Right | Left | Average |
| Control Placebo | 1.72 | 1.81 | 1.76 | 206.3 | 210.9 | 208.60 | 72.9 | 74.6 | 73.75 |
| 25 mg | 4.59 | 5.00 | 4.80 | 132.0 | 116.0 | 124.00 | 16.4 | 11.8 | 14.10 |
| 30 mg | 5.57 | 5.50 | 5.53 | 112.4 | 115.1 | 113.75 | 8.9 | 5.5 | 7.20 |
| 35 mg | 5.96 | 6.04 | 6.00 | 123.3 | 124.8 | 124.05 | 11.0 | 9.6 | 10.30 |

As compared to control placebo, the diameter of the seminiferous tubules and height of germinal epithelium decreased while the thickness of the basement membrane increased, and the differences were significant (p=0.0001)

In conclusion, one intratesticular injection of zinc gluconate neutralized by arginine at the dorsal cranial area of the testes of male puppies results in permanent sterilization of the male dog.

EXAMPLE 6

Four hundred fifty (450) intratesticular injections were performed in the dorsal cranial area of the testes of 225 male puppies (one injection per testis; two testes per dog) at five investigational sites. The 225 puppies ranged in age from 2½ to 10 months and were of various breeds. After the necessary training, all of the investigators mastered the technique of testicular measurement and intratesticular injection (dorsal cranial). Based on the experience of these investigators in the clinical trial, all veterinarians will be able to easily use this dorsal cranial injection technique.

After at least 6 months of follow-up, semen analysis and physical examination were performed as the primary indicators of clinical trial efficacy. The results showed that intratesticular injection at the dorsal cranial area of the testes with six (6) different doses achieved infertility/sterility in 224 of 225 puppies which reflects 99.6% efficacy.

Semen analysis is presented in the following table.

TABLE 6

Semen Analysis for All Five Investigational Sites Combined (n = 225 male puppies)

| Dose Per Testis (ml) | Aspermia (No Semen Ejaculated) | Azoospermia (No Sperm in Ejaculate) | Necrospermia (Sperm in Ejaculate Are Dead or Motionless) | Oligospermia (Less than 20 Million Sperm per ml) | Sperm in Ejaculate Are Motile |
|---|---|---|---|---|---|
| 0.2 | 59 | 12 | 0 | 1 | 0 |
| 0.3 | 27 | 5 | 0 | 0 | 0 |
| 0.5 | 21 | 7 | 0 | 0 | 1* |
| 0.7 | 30 | 4 | 0 | 0 | 0 |
| 0.8 | 19 | 4 | 1 | 0 | 0 |
| 1.0 | 18 | 16 | 0 | 0 | 0 |
| Total | 174 | 48 | 1 | 1 | 1 |

*Volume: 2.5 ml Motility: 80% Concentration/ml: $49 \times 10^6$

EXAMPLE 7

One hundred six (106) intratesticular injections of zinc gluconate neutralized by arginine were performed in the dorsal cranial area of the testes of 53 sexually mature, male dogs (one injection per testis; two testes per dog) ranging in age from one year to 12 years of age. Dosage was based on testicular width according to the following table.

TABLE 7

Dose Corresponding to Testicular Width

| Range of Testicular Width (mm) | Dose Administered (ml) |
| --- | --- |
| 10-12 | 0.2 |
| 13-15 | 0.3 |
| 16-18 | 0.5 |
| 19-21 | 0.7 |
| 22-24 | 0.8 |
| 25-27 | 1.0 |

Semen analysis of all dogs prior to injection indicated normal fertility parameters. All of the dogs were followed for six months post-injection, and semen analysis was performed at 2 month intervals for a total of three times. Results are shown in the following table.

TABLE 8

Semen Evaluation of Sexually Mature, Male Dogs Six Months Post-Injection (n = 53)

| Sperm Concentration | Dogs (n) |
| --- | --- |
| Azoospermia | 42 |
| Aspermia | 10 |
| Normal 70 million/ml | 1 |

Infertility/sterility was achieved in fifty-two (52) of fifty-three (53) dogs.

In view of the above, it will be seen that the several objects of the invention are achieved and other advantageous results attained. As various changes could be made in the above methods without departing from the scope of the invention, it is intended that all matter contained in the above description or shown in the accompanying drawings shall be interpreted as illustrative and not in a limiting sense.

Cited Literature

Andersson, H., Wallgren, M., Rydhmer, L., Lundstrom, K. Andersson, K. and Forsberg, M. 1998. Photoperiodic effects on pubertal maturation of spermatogenesis, pituitary responsiveness to exogenous GnRH, and expression of boar taint in crossbred boars. Anim Reprod Sci 54(2): 121-37.

Andersson, H., Rydhmer, L., Lundstron, K., Wallgren, M., Andersson, K. and Forsberg, M. 1998. Influence of artificial light regimens on sexual maturation and boar taint in entire male pigs. Anim Reprod Sci 51(1):31-43.

Anonymous. 2006. Prevention of boar taint in pig production. Abstracts of the 19th Symposium of the Nordic Committee for Veterinary Scientific Cooperation, Gardermoen, Norway, 21-22 Nov. 2005. Acta Vet Scand 48 Suppl 1:P1-6, S1-16.

Babol, J., Squires, E. J. and Lundstrom, K. 1999. Relationship between metabolism of androstenone and skatole in intact male pigs. J Anim Sci 77(1):84-92.

Babol, J., Squires, E. J. and Lundstrom, K. 1998. Relationship between oxidation and conjugation metabolism of skatole in pig liver and concentrations of skatole in fat. J Anim Sci 76(3):829-38.

Babol, J., Squires, E. J. and Lundstrom, K. 1998. Hepatic metabolism of skatole in pigs by Cytochrome P4502E1. J Anim Sci 76(3):822-8.

Babol, J., Squires, E. J. and Bonneau, M. 1996. Factors regulating the concentrations of 16-androstene steroids in submaxillary salivary glands of pigs. J Anim Sci 74(2):413-9.

Beery, K. E. and J. D. Sink. 1971. Isolation and identification of 3alpha-hydroxy-5alpha-androst-16-ene- and 5alpha-androst-16-en-3-one from porcine tissue. J Endocrinol 51:223.

Beery, K. E., J. D. Sink, S. Patton and J. H. Ziegler. 1971. Characterization of the swine sex odor (SSO) components in boar fat volatiles. J Food Sci 36:1086.

Berger, T., K. L. Esbenshade, M. A. Diekman, T. Hoagland and J. Tuite. 1981. Influence of prepubertal consumption of zearalenone on sexual development of boars. J Anim Sci 53:1559.

Bierschwal, C. J. and E. F. Ebert. 1961. Clinical applications of a sclerotherapeutic agent. Vet Med 56:323.

Bonneau, M., Dufour, R., Chouvet, C., Roulet, C., Meadus, W. and Squires, E. J. 1994. The effects of immunization against luteinizing hormone-releasing hormone on performance, sexual development, and levels of boar taint-related compounds in intact male pigs. J Anim Sci 72(1):14-20.

Bonneau, M. and M. Terqui. 1982. A note on the metabolism of 5alpha-androst-16-en-3-one in the young boar in vivo. Reprod Nutr Dev 23:899.

Bonneau, M. 1981. Endocrinological and physical aspects of boar taint. Conference Report On Boar Taint, 1981, Zeist. Livest Prod Sci 8:573.

Brooks, R. I. and A. M. Pearson. 1989. Odor thresholds of the C19-Steroids responsible for boar odor in pork. Meat Sci 24:11.

Brooks, R. I., A. M. Pearson, M. G. Hogberg, J. J. Pestka and J. I. Gray. 1986. An immunological approach for prevention of boar odor in pork. J Anim Sci 62:1279.

Claus, R. 1976. Messung des Ebergeruchstoffes im Fett von Schweinen mittels eines Radioimmunotests. II. Zeitlecher Verlauf des Geruchdepotabbaues nach der kastration. Z Tierz Zuchtungsbiol 93:38.

Claus, R. 1979. Pheromone bei Suagetieren unter besonderer Berucksichtigung des Ebergeruchsstoffes und seiner Beziehung zu anderen Hodensteroiden. Z Tierphysiol Tierernahr Futtermittelkd 10:1.

Davis, S. M. and Squires, E. J. 1999. Association of cytochrome b5 with 16-androstene steroid synthesis in the testis and accumulation in the fat of male pigs. J Anim Sci 77(5):1230-5.

Diaz, G. J. and Squires, E. J. 2000. Metabolism of 3-methylindole by porcine liver microsomes: responsible cytochrome P450 enzymes. J Toxicol Sci 55(2):284-92.

Doran, E., Whittington, F. M., Wood, J. D. and McGivan, J. D. 2004. Characterisation of androstenone metabolism in pig liver microsomes. Chem Biol Interact 147(2):141-9.

Doran, E., Whittington, F. W., Wood, J. D. and McGivan, J. D. 2002. Cytochrome P450IIE1 (CYP2E1) is induced by skatole and this induction is blocked by androstenone in isolated pig hepatocytes. Chem Biol Interact 140(1):81-92.

Dunshea, F. R., Colantoni, C., Howard, K., McCauley, I., Jackson, P., Long, K. A., Lopaticki, S., Nugent, E. A., Simons, J. A., Walker, J. and Hennessy, D. P. 2001. Vaccination of boards with a GnRH vaccine (Improvac) eliminates boar taint and increases growth performance. J Anim Sci 79(10):2524-35.

Freeman, C. and D. S. Coffey. 1973. Sterility in male animals induced by injection of chemical agents into the vas deferens. Fertil Steril 24:884.

Giersing, M., Lundstrom, K. and Andersson, A. 2000. Social effects and boar taint: significance for production of slaughter boars (Sus scrofa). J Anim Sci 78(2):296-305.

Gower, D. B. 1972. 16-unsaturated $C_{19}$ steroids. A review of their chemistry, biochemistry and possible physiological role. J Steroid Biochem 3:45.

Hansen-Moller, J. 1994. Rapid high-performance liquid chromatographic method for simultaneous determination of androstenone, skatole and indole in back fat from pigs. J Chromatogr B Biomed Appl 661(2):219-30.

Hansson, K. E., K. Lundstrom, S. Fjelkner-Modig, and J. Persson. 1980. The importance of androstenone and skatole for boar taint. Swed J Agric Res 10:167.

Heinritzi, K., Ritzman, M. and Otten. W. 2006. [Alternatives for castration of suckling piglets, determination of catecholamines and wound healing after castration of suckling piglets at different points of time]. [German] DTW—Deutsche Tierarztliche Wochenschrift 113(3):94-7.

Hines, R. H., J. A. Hoefer, R. A. Merkel and E. R. Miller. 1969. Influences of restricted feeding and sex upon performance and carcass quality. Michigan Swine Research Report. 99:53.

Hunter, R. H. and Greve, T. 1996. Intersexuality in pigs: clinical, physiological and practical considerations. Acta Vet Scand 37(1):1-12.

Jonsson, P. and O. Andresen. 1979. Experience during two generations of within-lines testing, using 5alpha-androst-16-ene-3-one (5alpha-androstenone) and an olfactory judgement of boar taint. Ann Genet Sel Anim 11:241.

Klindt, J., Buonomo F. C., Yen J. T. and Baile C. A. 1995. Growth performance, carcass characteristics, and sensory attributes of boars administered porcine somatotropin by sustained-release implant for different lengths of time. J Food Sci 73(12):3585-95.

Klindt, J., Buonomo, F. C. and Yen, J. T. 1995. Administration of porcine somatotropin by sustained-release implant: growth, carcass, and sensory responses in crossbred white and genetically lean and obese boars and gilts. J Food Sci 73(5):1327-39.

Kluber, E. F., III, J. E. Minton, J. S. Stevenson, M. C. Hunt, D. L. Davis, T. A. Hoagland and J. L. Nelssen. 1988. Growth, carcass traits, boar odor and testicular and endocrine functions of male pigs fed a progestogen, altrenogest. J Anim Sci 66:470.

Kuhlers, P. L., L. L. Christian and H. H. Lsou. 1976. Performance differences between boars and barrows taken to heavier weights. Duroc News. 50:301.

Lanthier, F., Lou, Y., Terner, M. A. and Squires, E. J. 2006. Characterizing developmental changes in plasma and tissue skatole concentrations in the prepubescent intact male pig. J Anim Sci 84(7):1699-708.

Lee, G. J., Archibald, A. L., Law, A. S., Lloyd, S., Wood, J. and Haley, C. S. 2005. Detection of quantitative trait loci for androstenone, skatole and boar taint in a cross between Large White and Meishan pigs. Anim Genet 36(1):14-22.

Lerche, H. 1936. Geschlechtsgeruch bei eberkastraten. Z Fleisch Milchhyg 46:417.

Lin, Z., Lou, Y. and Squires, E. J. 2006. Functional polymorphism in porcine CYP2E1 gene: Its association with skatole levels. J Steroid Biochem Mol Biol 99(4-5):231-7.

Lin, Z., Lou, Y., Peacock, J. and Squires, E. J. 2005. A novel polymorphism in the 5' untranslated region of the porcine cytochrome b5 (CYB5) gene is associated with decreased fat androstenone level. Mamm Genome 16(5):367-73.

Lin, Z., Lou, Y. and Squires, E. J. 2004. Molecular cloning, expression and functional characterization of the cytochrome P450 2A6 gene in pig liver. Anim Genet 35(4):314-6.

Lin, Z., Lou, Y. and Squires, J. E. 2004. Molecular cloning and functional analysis of porcine SULT1A1 gene and its variant: a single mutation SULT1A1 causes a significant decrease in sulfation activity. Mamm Genome 15(3):218-26.

Lundstrom, K., B. Malmfors, G. Malmfors, S. Stern, H. Petersson, A. B. Mortensen, and S. E. Sorensen. 1988. Skatole, androstenone and taint in boars fed two different diets. Livest Prod Sci 18:55.

Malaviya, B., H. Chandra, and A. B. Kar. 1974. Chemical occlusion of vas deferens by quinacrine in rhesus monkeys. Indian J Exp Biol 62:560.

Malmfors, B. and K. Lundstrom. 1983. Consumer reactions to boar meat: A review. Livest Prod Sci 10:187.

Meloen, R. H., Turkstra, J. A., Lankhof, H., Puijk, W. C., Schaaper, W. M., Dijkstra, G, Wensing, C. J. and Oonk, R. B. 1994. Efficient immunocastration of male piglets by immunoneutralization of GnRH using a new GnRH-like peptide. Vaccine 12(8):741-6.

Mortensen, A. B., C. Bejerholm, and J. K. Pedersen. 1986. Consumer test of meat from entire males, in relation to skatole in backfat. Proc. 32nd European Meeting of Meat Research Workers, Ghent, 23-26.

Oonk, H. B., Turkstra, J. A., Schaaper, W. M., Erkens, J. H., Schuitemaker-de Weerd, M. H., van Nes, A., Verheijden, J. H. and Meloen, R. H. 1998. New GnRH-like peptide construct to optimize efficient immunocastration of male pigs by immunoneutralization of GnRH. Vaccine 16(11-12):1074-82.

Patterson, R. L. S. 1968. 5alpha-androst-16-ene-3-one: Compound responsible for taint in boar fat. J Sci Food Agric 19:31.

Pineda, M. H., T. J. Reimers, L. C. Faulkner, M. L. Hopwood, and G. E. Seidel. 1976. Azoospermia in dogs induced by injection of sclerosing agents into the caudae of the epididymides. Am J Vet Res 38:831.

Rius Sole, M. A. and Garcia Regueiro, J. A. 2001. Role of 4-phenyl-32-buten-2-one in boar taint: identification of new compounds related to sensorial descriptors in pig fat. J Agric Food Chem 49(11):5303-9.

Scaramuzzi, R. J., Campbell, B. K. and Martin, G. B. 1993. Immunological approaches to fertility regulation in domestic livestock. Immunol Cell Biol 71(Pt5):489-99.

Schneider, F., Falkenberg, H., Kuhn, G., Nurnberg, K., Rehfeldt, C. and Kanitz, W. 1998. Effects of treating young boars with a GnRH depot formulation on endocrine functions, testis size, board taint, carcass composition and muscular structure. Anim Reprod Sci 50(1-2):69-80.

Sinclair, P. A., Gilmore, W. J., Lin, Z., Lou, Y. and Squires, E. J. 2006. Molecular cloning and regulation of porcine SULT2A1 relationship between SULT2A1 expression and sulfoconjugation of androstenone. J Mol Endocrinol 36(2):301-11.

Sinclair, P. A., Squires, E. J., Raeside, J. I. and Renaud, R. 2005. Synthesis of free and sulphoconjugated 16-androstene steroids by the Leydig cells of the mature domestic boar. J Steroid Biochem Mol Biol 96(2):217-28.

Sinclair, P. A., Squires, E. J. and Raeside, J. I. 2001. Early postnatal plasma concentrations of testicular steroid hormones, pubertal development, and carcass leanness as potential indicators of boar taint in market weight intact male pigs. J Anim Sci 79(7):1868-76.

Skinner, T. M., Doran, E., McGivan, J. D., Haley, C. S. and Archibald, A. L. 2005. Cloning and mapping of the porcine cytochrome-p450 2E1 gene and its association with skatole levels in the domestic pig. Anim Genet 36(5):417-22.

Stolle, A., Sedlmeier, H. and Wirrer, B. 1994. [The efficiency of photometric determination of skatole in slaughtered swine]. [German] Zeitschrift fur Lebensmittel-Untersuchung und -Forschung. 199(4):301-6.

Squires, E. J., Gullett, E. A., Fisher, K. R. and Partlow, G. D. 1991. Comparison of androst-16-ene steroid determined by a colorimetric assay with boar taint estimated by a trained sensory panel. J Anim Sci 69(3):1092-100.

Terner, M. A., Gilmore, W. J. and Squires, E. J. 2006. The role of CYP2A and CYP2E1 in the metabolism of 3-methylindole in primary cultures porcine hepatocytes. Drug Metab Dispos 34(5):848-54.

Treyer, V., Koch, H., Briner, H. R., Jones, N. S., Buck, A. and Simmen, D. B. 2006. Males subjects who could not perceive the pheromone 5a-androst-16-en-3-one, produced similar orbitofrontal changes on PET compared with perceptible phenylethyl alcohol. Rhinology 44(4):278-82.

VanDerMark, P. K. and Steggles, A. W. 1997. The isolation and characterization of the soluble and membrane-bound porcine cytochrome b5 cDNAs. Biochem Biophys Res Commun 240(1):80-3.

Vold, E. 1970. Fleischproduktionseigenschaften bei Ebern und Kastraten. IV. Organoleptische und gaschromatographische Untersuchungen wasserdampfflüchtiger Stoffe des Ruckenspeckes von Ebern. Report No. 238. Institute of Animal Genetics and Breeding, NLH, Vollebekk. 25.

Walstra, P. 1984. Analytical methods for determination of boar taint. Report From the E. A. A. P. Working Group Meeting, October 1984, Holbaek. Livest Prod Sci 13:303.

Walstra, P. and H. Maarse. 1970. Onderzoek geslachtsgeur van mannelijke mestvarkens. I. V. O. -Rapport C-147 and Rapport No. 2. Researchgroip Vlees en Vleeswren T. N. O., Zeist, 30.

Wang, C. Y. and Walfield, A. M. 2005. Site-specific peptide vaccines for immunotherapy and immunization against chronic disease, cancer, infectious diseases, and for veterinary applications. Vaccine 23(17-18):2049-56.

Willeke, H. 1980. A selection experiment against 5alpha-Androst-16-en-3-one, the boar taint steroid, in adipose tissue of boars. Z. Tierzuchtg Zuchtungsbiol 97:86.

Williamson, E. D., R. L. S. Patterson, E. R. Buxton, K. G. Mitchell, I. G. Partridge and N. Walker. 1985. Immunization against 5alpha-androstenone in boars. Livest Prod Sci 12:251.

Wood, J. D. and J. E. Riley. 1982. Comparison of boars and castrates for bacon production. 1. Growth data, and carcass joint composition. Anim Prod 35:55.

Xue, J. L., Dial, G. D., Bartsh, S., Kerkaert, B., Squires, E. J., Marsh, W. E. and Ferre, G. 1994. Influence of a gonadotropin-releasing hormone agonist on circulating concentrations of luteinizing hormone and testosterone and tissue concentrations of compounds associated with boar taint. J Anim Sci 72(5):1290-8.

Xue, J., Dial, G. D., Holton, E. E., Vickers, Z., Squires, E. J., Lou, Y., Godbout, D. and Morel, N. 1996. Breed differences in boar taint: relationship between tissue levels boar taint compounds and sensory analysis of taint. J Anim Sci 74(9):2170-7.

Yokoyama, M. T. and J. R. Carlson. 1979. Microbial metabolites of tryptophan in the intestinal tract with special reference to skatole. Am J Clin Nutr 32:173.

Zamaratskaia, G., Rydhmer, L., Chen, G., Madej, A., Andersson, H. K. and Lundstrom, K. 2005. Boar taint is related to endocrine and anatomical changes at puberty but not aggressive behaviour in entire male pigs. Reprod Domest Anim 40(6):500-6.

Zamaratskaia, G., Madej, A., Babol, J., Squires, E. J. and Lundstrom, K. 2005. Free oestrone in adipose tissue and its relation to androstenone and skatole in entire male pigs. Reprod Domest Anim 40(2):156-60.

Zamaratskaia, G., Babol, J., Madej, A., Squires, E. J. and Lundstrom, K. 2004. Age-related variation of plasma concentrations of skatole, androstenone, testosterone, oestradiol-17 beta, oestrone sulphate, dehydroepiandrosterone sulphate, triiodothyronine and IGF-1 in six entire male pigs. Reprod Domest Anim 39(3):168-72.

What is claimed:

1. A method for improving the quality of meat by reducing boar taint, said method comprising locating a head of an epididymis in each testis of a male pig and injecting a solution of a water soluble pharmaceutically acceptable zinc salt containing at least 20 mg of zinc ion per 1 ml of solution, said injection into a dorsal cranial portion of the testis beside the head of the epididymis, said solution having a pH in the range of 6.0 to 7.5 and injected in a volume that is contained within the testis and that has sufficient zinc ion to suppress the production of skatole and androstenone, said injection at least one day prior to slaughtering the animal and resulting in proportionate shrinkage of the testis.

2. The method of claim 1 wherein the pig less than seven days old and the solution injected into each testis contains between about 10 and 30 mg of zinc ion in volume between about 0.1 and 0.5 ml.

3. The method of claim 1 wherein the pig no more than three days old and the solution injected into each testis contains about 20 mg of zinc ion in volume between about 0.2 and 0.4 ml.

4. The method of claim 1 wherein the zinc salt has an LD50 of more than 500 mg/kg in rats.

5. The method of claim 3 wherein the zinc salt is derived from a carboxylic acid.

6. The method of claim 5 wherein the zinc salt is zinc acetate or zinc propionate.

7. The method of claim 5 wherein the zinc salt is zinc acetate.

8. The method of claim 1 wherein the amount of zinc ion injected into each testis is between about 50 and 150 mg when the pig is about 4 weeks old.

9. The method of claim 1 wherein the amount of zinc ion injected into each testis is between about 250 and 800 mg when the pig is a mature boar.

* * * * *